(12) United States Patent
Jung et al.

(10) Patent No.: US 11,779,229 B2
(45) Date of Patent: Oct. 10, 2023

(54) ELECTRONIC DEVICE CAPABLE OF MEASURING BLOOD PRESSURE AND METHOD FOR MEASURING BLOOD PRESSURE THEREBY

(71) Applicant: Samsung Electronics Co., Ltd., Gyeonggi-do (KR)

(72) Inventors: Sunok Jung, Gyeonggi-do (KR); Daniel Joe, Gyeonggi-do (KR); Minhyun Cho, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 205 days.

(21) Appl. No.: 17/071,089

(22) Filed: Oct. 15, 2020

(65) Prior Publication Data

US 2021/0113103 A1    Apr. 22, 2021

(30) Foreign Application Priority Data

Oct. 18, 2019   (KR) ........................ 10-2019-0129959

(51) Int. Cl.
    *A61B 5/021*    (2006.01)
    *A61B 5/00*     (2006.01)

(52) U.S. Cl.
    CPC ........ *A61B 5/02141* (2013.01); *A61B 5/0059* (2013.01); *A61B 5/681* (2013.01); *A61B 5/72* (2013.01); *A61B 5/742* (2013.01)

(58) Field of Classification Search
    CPC ... A61B 5/02141; A61B 5/0059; A61B 5/681; A61B 5/72; A61B 5/742; A61B 5/02225;
    (Continued)

(56) References Cited

U.S. PATENT DOCUMENTS

2012/0190944 A1   7/2012   Thaveeprungsriporn et al.
2014/0296658 A1   10/2014  Yuen et al.
(Continued)

FOREIGN PATENT DOCUMENTS

EP    3469984 A1      4/2019
JP    2014-507209 A   3/2014
(Continued)

OTHER PUBLICATIONS

Extended European Search Report dated Jul. 15, 2022.
(Continued)

*Primary Examiner* — Eric F Winakur
*Assistant Examiner* — Abid A Mustansir
(74) *Attorney, Agent, or Firm* — Cha & Reiter, LLC

(57) ABSTRACT

An electronic device and method are disclosed herein. The electronic device includes a display, a printed circuit board (PCB) disposed below the display and having a first surface facing the display, a biometric sensor disposed on the first surface of the PCB and configured to measure a biometric signal related to a heartbeat, a pressure sensor disposed below the display and configured to generate a pressure signal based on measuring a pressure applied to the display, a processor. The processor implements the method, including measuring, by the biometric sensor, the biometric signal, measuring, by the pressure sensor, the pressure applied to the display, calculating biometric information related to a heartbeat by interlinking the biometric signal and the pressure signal, and outputting the calculated biometric information to the display.

17 Claims, 14 Drawing Sheets

(58) Field of Classification Search
CPC .......... A61B 5/02241; A61B 5/02422; A61B 5/7235; A61B 5/7435; A61B 5/02116; A61B 5/02438; A61B 2562/0247; A61B 2562/166; A61B 5/02108; A61B 5/743; A61B 5/7445

See application file for complete search history.

(56) References Cited

U.S. PATENT DOCUMENTS

| | | | |
|---|---|---|---|
| 2016/0166197 A1* | 6/2016 | Venkatraman | A61B 5/0816 600/595 |
| 2017/0095168 A1 | 4/2017 | Kwon et al. | |
| 2017/0251935 A1* | 9/2017 | Yuen | A61B 5/0295 |
| 2018/0256036 A1 | 9/2018 | Kogure et al. | |
| 2019/0008399 A1 | 1/2019 | Mukkamala et al. | |
| 2019/0104997 A1 | 4/2019 | Kang et al. | |
| 2021/0137446 A1* | 5/2021 | Brownhill | A61B 5/683 |

FOREIGN PATENT DOCUMENTS

| | | |
|---|---|---|
| KR | 10-2006-0081178 A | 7/2006 |
| KR | 10-2017-0019882 A | 2/2017 |

OTHER PUBLICATIONS

Anad Chandrasekhar et al: "Smartphone-based blood pressure monitoring via the oscillometric finger-pressing method", Science Translational Medicine, vol. 1, No. 431, Mar. 7, 2018, p. eaap 8674.

International Search Report dated Jan. 15, 2021.

Anand Chandrasehar et al.; "Smartphone-based blood pressure monitoring via the oscillometric finger-pressing method"; Sci Transl Med. Mar. 7, 2018; pp. 1-24.

* cited by examiner

FIG. 7B
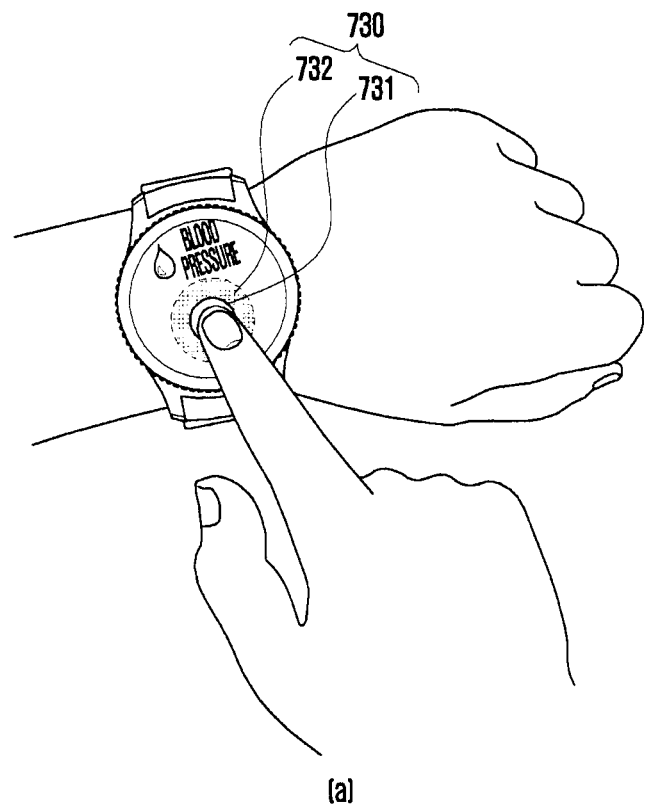
(a)
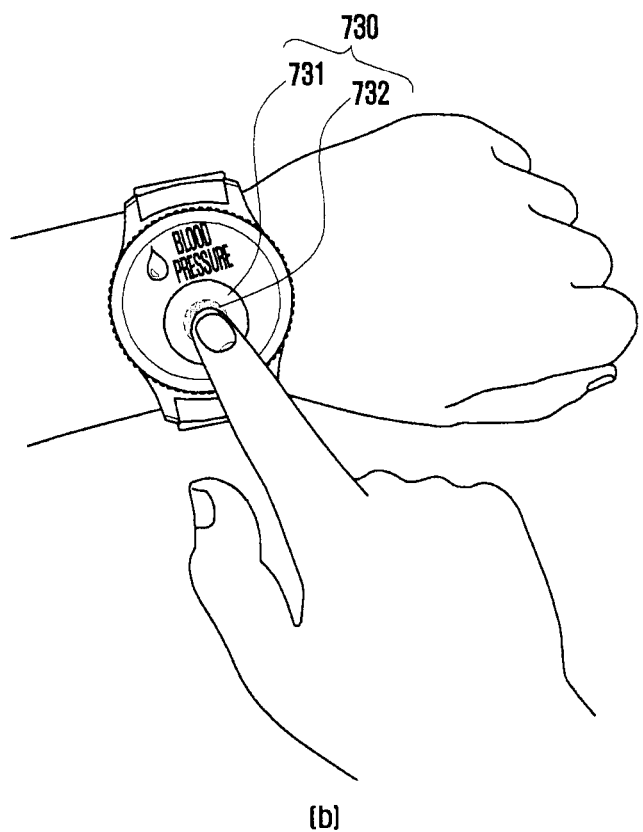
(b)

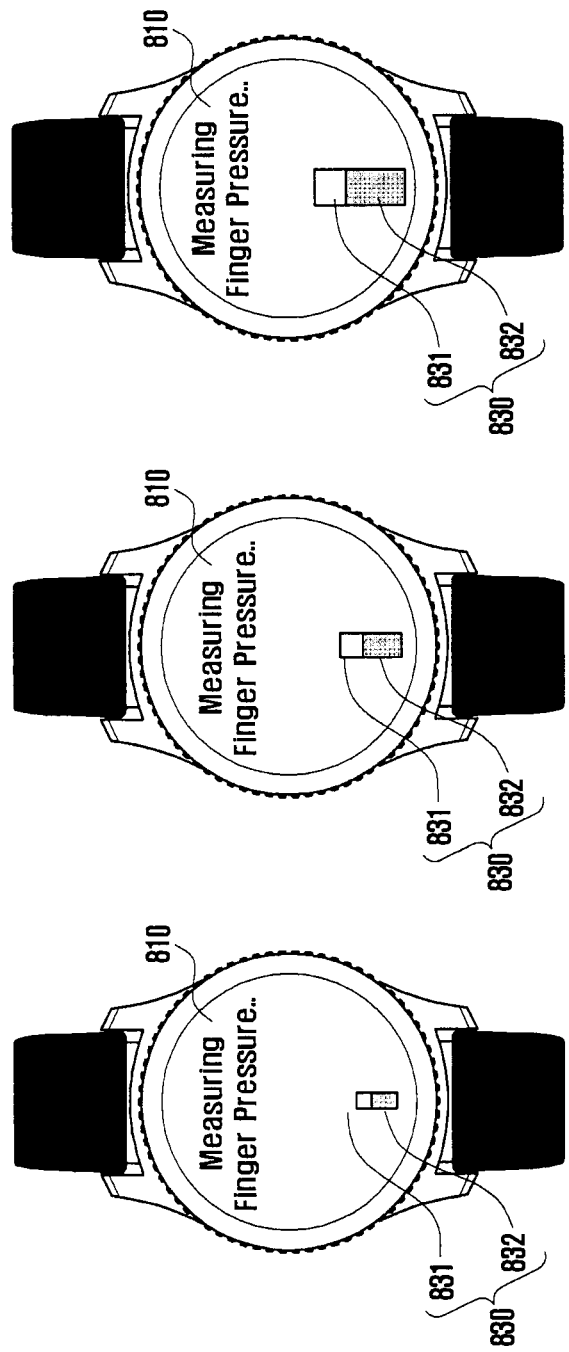

ELECTRONIC DEVICE CAPABLE OF MEASURING BLOOD PRESSURE AND METHOD FOR MEASURING BLOOD PRESSURE THEREBY

CROSS-REFERENCE TO RELATED APPLICATION(S)

This application is based on and claims priority under 35 U.S.C. 119 to Korean Patent Application No. 10-2019-0129959, filed on Oct. 18, 2019, in the Korean Intellectual Property Office, the disclosure of which is herein incorporated by reference in its entirety.

BACKGROUND

1) Field

Certain embodiments disclosed in this document relate to electronically-enabled detection of blood pressure, and more particular, to using a smart-device including an under-display pressure sensor and biometric sensor to detect blood pressure.

2) Description of Related Art

Electronic devices are often now equipped with sensors and functions capable of detecting biometrics. Wristwatch-type wearable electronic devices, for example, are often equipped with biometric sensors.

One type of biometric detection undergoing rapid development is the noninvasive measurement of blood-pressure, which are far more convenient than conventional blood pressure gauges that use a cuff. In contrast, noninvasive blood-pressure measurement methods are practically applicable to electronic devices because no cuff is used.

Non-invasive blood-pressure measurements techniques may be applied to an electronic device, allowing measurement of the user's blood pressure without a cuff.

The above information is presented as background information only to assist with an understanding of the disclosure. No determination has been made, and no assertion is made, as to whether any of the above might be applicable as prior art with regard to the disclosure.

SUMMARY

One non-invasive method for detecting blood pressure involves detecting a change in a pulse wave following an applied pressure. However, typically in these measurements, the applied pressure needs to be increased/decreased to a predetermined level.

Certain embodiments disclosed in this document provide an electronic device capable of inducing the user to apply a pressure that increases/decreases to a predetermined level, and a corresponding method for measuring blood pressure thereby.

In an embodiment of the disclosure, an electronic device is disclosed, including a display, a printed circuit board (PCB) disposed below the display and having a first surface facing the display, a biometric sensor disposed on the first surface of the PCB and configured to measure a biometric signal related to a heartbeat, a pressure sensor disposed below the display and configured to generate a pressure signal based on measuring a pressure applied to the display, a processor operatively connected to the display, the biometric sensor, and the pressure sensor, and a memory operatively connected to the processor, such that the memory stores instructions that, when executed, cause the processor to: measure, by the biometric sensor, the biometric signal, measure, by the pressure sensor, the pressure applied to the display, calculate biometric information related to a heartbeat by interlinking the biometric signal and the pressure signal, and output the calculated biometric information to the display.

In an embodiment of the invention, a method in an electronic device is disclosed, including: measuring, using a pressure sensor, a pressure signal based on pressure applied to a display, displaying, using a display, a visual guide prompting a user generating the pressure to gradually increase and decrease the pressure, while the pressure gradually increases and decreases, measuring a change in a biometric signal related to a heartbeat using a biometric sensor, including a pulse wave signal, detecting a change in the pulse wave signal while the pressure gradually increases and decreases; and calculating the user's blood pressure based on the detected change in the pulse wave signal while the pressure gradually increases and decreases.

According to certain embodiments disclosed in this document, the user may intuitively identify the pressure applied to the electronic device.

In addition, the user may be induced to apply a pressure to the electronic device, the pressure increasing/decreasing to a specific level, thereby enabling accurate blood pressure measurement.

BRIEF DESCRIPTION OF THE DRAWINGS

For a more complete understanding of the disclosure and its advantages, reference is now made to the following description taken in conjunction with the accompanying drawings, in which like reference numerals represent like parts:

FIG. 7B(a) is a diagram for describing a visual guide of an electronic device according to certain embodiments, and FIG. 7B(b) is a diagram for describing a visual guide of an electronic device according to certain embodiments;

FIG. 8(a) is a diagram for describing a visual guide of an electronic device according to certain embodiments, FIG. 8(b) is a diagram for describing a visual guide of an electronic device according to certain embodiments, and FIG. 8(c) is a diagram for describing a visual guide of an electronic device according to certain embodiments;

DETAILED DESCRIPTION

Figure 1:
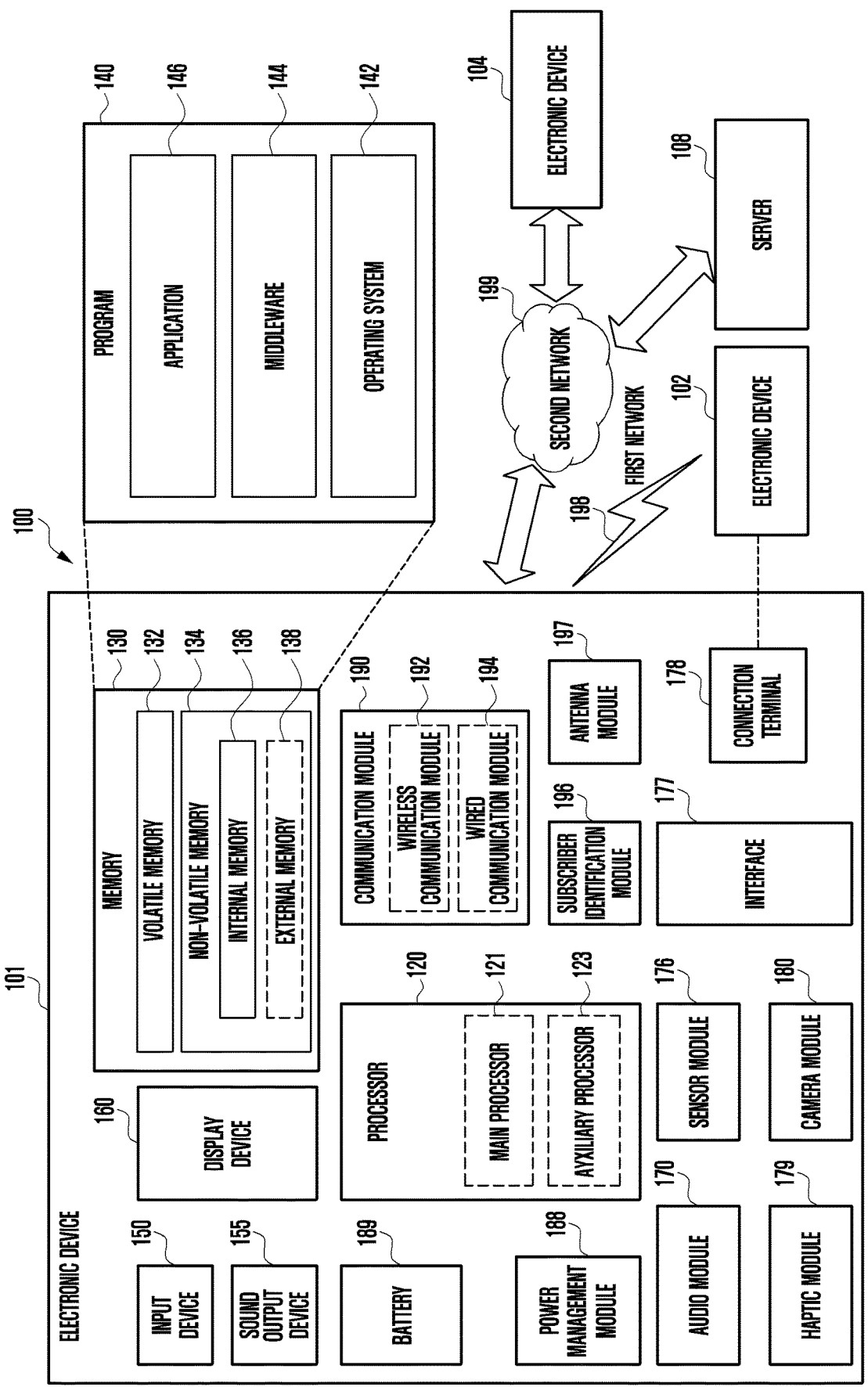
FIG. 1 is a block diagram of an electronic device inside a network environment according to certain embodiments.

FIG. 1 is a block diagram illustrating an electronic device 101 in a network environment 100 according to certain embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134 which may include internal memory 136 and/or external memory 138. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element implemented using a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
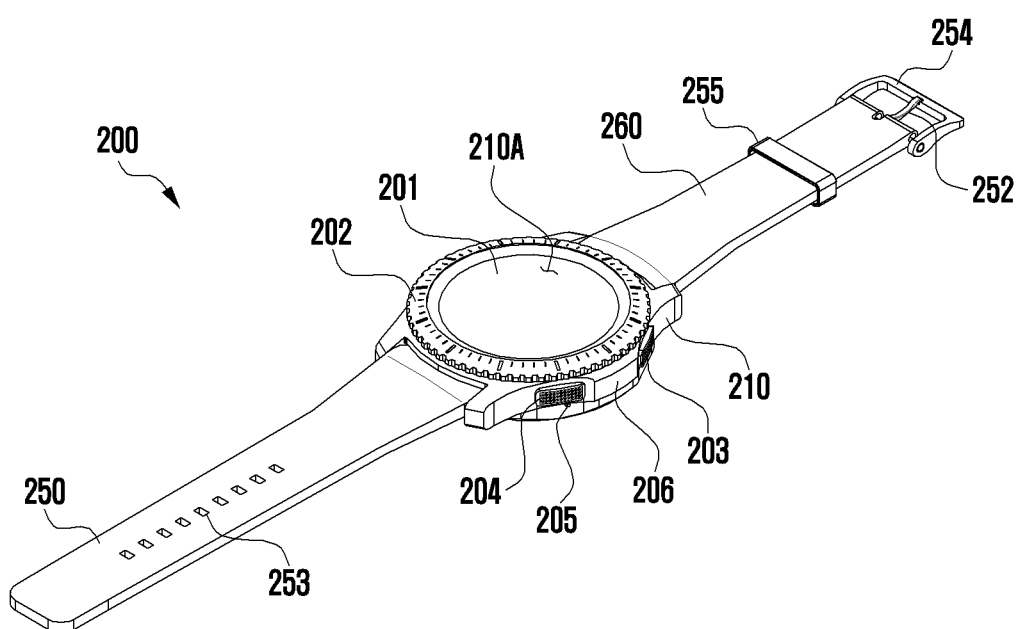
FIG. 2 is a front perspective view of a mobile electronic device according to certain embodiments disclosed in this document.
Figure 3:
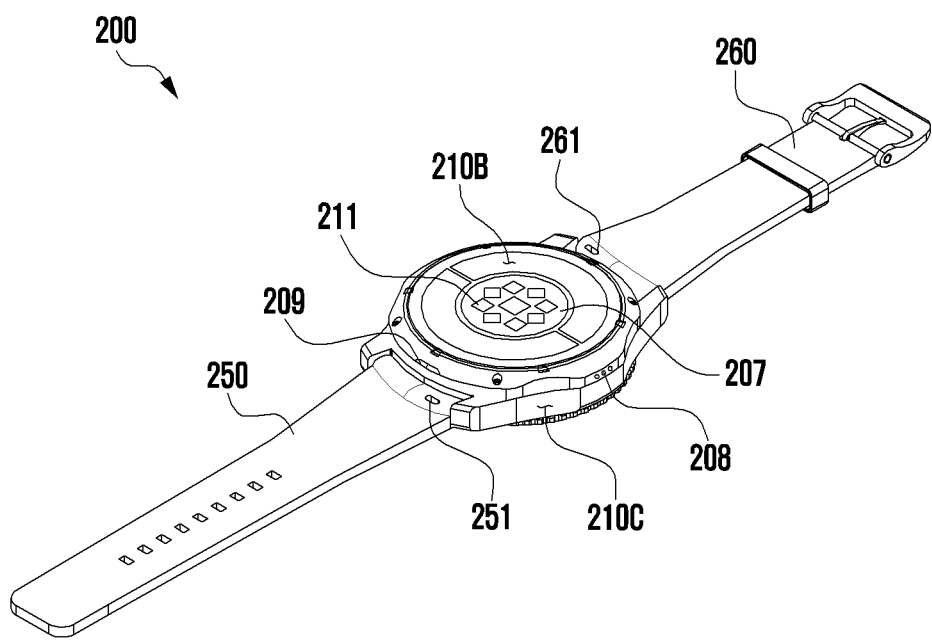
FIG. 3 is a rear perspective view of the electronic device in FIG. 2.
Figure 4:
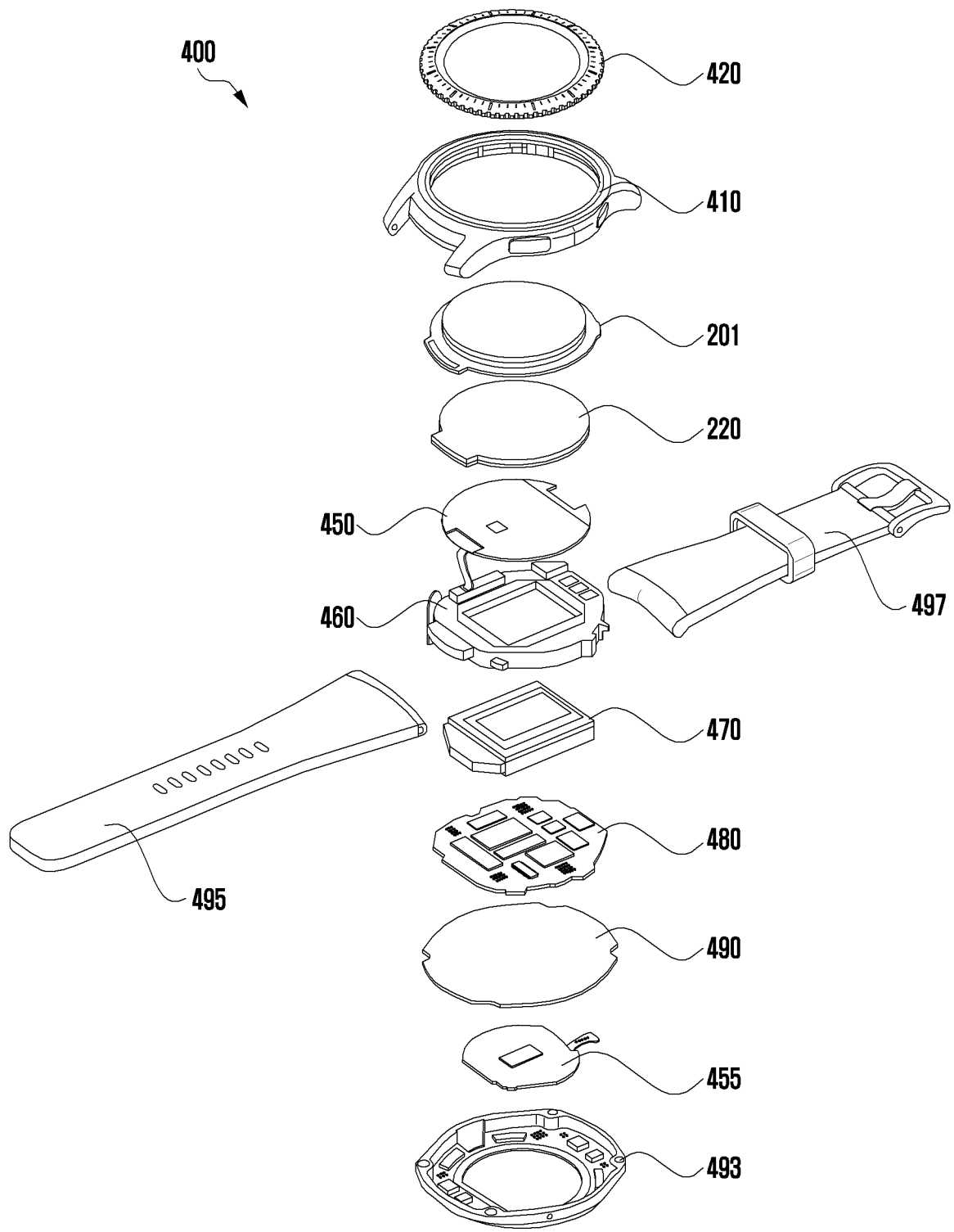
FIG. 4 is an exploded perspective view of the electronic device in FIG. 2.

FIG. 2 is a front perspective view of a mobile electronic device according to certain embodiments disclosed in this document. FIG. 3 is a rear perspective view of the electronic device in FIG. 2. FIG. 4 is an exploded perspective view of the electronic device in FIG. 2.

Referring to FIG. 2 and FIG. 3, the electronic device 200 according to an embodiment may include: a housing 210 including a first surface (or front surface) 210A, a second surface (or rear surface) 210B, and a side surface 210C surrounding the space between the first surface 210A and the second surface 210B; and clamping members 250 and 260 connected to at least a part of the housing 210 and configured such that the electronic device 200 is clamped to a part of the user's body (for example, the wrist, ankle, or the like) in an attachable/detachable manner. In another embodiment (not illustrated), the housing may refer to a structure forming at least some of the first surface 210A, the second surface 210B, and the side surface 210C in FIG. 2. According to an embodiment, the first surface 210A may be formed by a front plate 201, at least a part of which is substantially transparent (for example, a glass plate including various coating layers, or a polymer plate). The second surface 210B may be formed by a rear plate 207 which is substantially opaque. The rear plate 207 may be made of, for example, coated or colored glass, ceramic, polymer, metal (for example, aluminum, stainless steel (STS), or magnesium), or a combination of at least two of the above materials. The side surface 210C may be formed by a side bezel structure (also referred to as "side member") 206, which is coupled to the front plate 201 and the rear plate 207, and which includes a metal and/or a polymer. In some embodiments, the rear plate 207 and the side bezel structure 206 may be formed integrally and made of the same material (for example, a metal material such as aluminum). The clamping members 250 and 260 may be made of various materials and in various types. The clamping members 250 and 260 may be made of a woven material, leather, rubber, urethane, metal, ceramic, or a combination of at least two of the above materials in an integrated type, and may be formed such that multiple unit links can move with regard to each other.

According to an embodiment, the electronic device 200 may include at least one of a display 220 (see FIG. 4), audio modules, a sensor module 211, key input devices 202, 203, and 204, and a connector hole 209. In some embodiments, at least one of the components of the electronic device 200 (for example, the key input devices 202, 203, and 204, the connector hole 209, or the sensor module 211) may be omitted, or other components may be further included.

The display 220 may be exposed through a corresponding part of the front plate 201, for example. The display 220 may have one of various shapes, such as a circle, an ellipse, or a polygon, which corresponds to that of the front plate 201. The display 220 may be coupled to or disposed adjacent to a touch sensing circuit, a pressure sensor capable of sensing the intensity (pressure) of a touch, and/or a fingerprint sensor.

The audio modules may include a microphone hole 205 and a speaker hole 208. The microphone hole 205 may have a microphone disposed therein so as to acquire an external sound, and may have multiple microphones disposed therein so as to sense the direction of the sound, in some embodiments. The speaker hole 208 may be used as an external speaker and a telephone speech receiver. In some embodiments, speaker holes 208 and a microphone hole 205 may be implemented as a single hole, or a speaker (for example, piezoelectric speaker) may be included without the speaker holes 208.

The sensor module 211 may produce an electric signal or a data value corresponding to the operating state inside the electronic device 200 or the environmental state outside the same. The sensor module 211 may include a biometric sensor module 211 (for example, an HRM sensor) disposed on the second surface 210B of the housing 210, for example. The electronic device 200 may further include a sensor module (not illustrated), for example, at least one of a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or an illuminance sensor.

The key input devices 202, 203, and 204 may include a wheel key 202 disposed on the first surface 210A of the housing 210 to be able to rotate in at least one direction and/or side key buttons 202 and 203 disposed on the side surface 210C of the housing 210. The wheel key may have a shape corresponding to that of the front plate 201. In another embodiment, the electronic device 200 may not include some or all of the above-mentioned key input devices 202, 203, and 204, and the key input devices 202, 203, and 204 that are not included may be implemented as other types (for example, soft keys) on the display 220. The connector hole 209 may include other connector holes (not illustrated) capable of containing a connector (for example, USB connector) for transmitting/receiving power and/or data to/from an external electronic device, and capable of containing a connector for transmitting/receiving audio signals to/from an external electronic device. The electronic device 200 may further include a connector cover (not illustrated) covering at least a part of the connector hole 209, for example, and preventing external foreign substances from entering the connector hole.

The clamping members 250 and 260 may be clamped to at least a partial region of the housing 210 in an attachable/detachable manner by using locking members 251 and 261. The clamping members 250 and 260 may include at least one of a fixing member 252, a fixing-member fastening hole 253, a band guide member 254, and a band-fixing ring 255.

The fixing member 252 may be configured to fix the housing 210 and the clamping members 250 and 260 to a part of the user's body (for example, the wrist, ankle, or the like). The fixing-member fastening hole 253 may correspond to the fixing member 252 such that the housing 210 and the clamping members 250 and 260 are fixed to a part of the user's body. The band guide member 254 may be configured to limit the range of movement of the fixing member 252 when the fixing member 252 is fastened to the fixing-member fastening hole 253, thereby enabling the clamping members 250 and 260 to be forced against and clamped to a part of the user's body. The band-fixing ring 255 may limit the range of movement of the clamping members 250 and 260 while the fixing member 252 and the fixing-member fastening hole 253 are fastened.

Referring to FIG. 4, the electronic device 400 may include a side bezel structure 410, a wheel key 420, a front plate 201, a display 220, a first antenna 450, a second antenna 455, a support member 460 (for example, a bracket), a battery 470, a printed circuit board 480, a sealing member 490, a rear plate 493, and clamping members 495 and 497. At least one component of the electronic device 400 may be identical or similar to at least one component of the electronic device 200 in FIG. 2 or FIG. 3, and a repeated description thereof will thus be omitted herein. The support member 460 may be disposed inside the electronic device 400 and connected to the side bezel structure 410, or may be formed integrally with the side bezel structure 410. The support member 460 may be made of a metal material and/or a nonmetal (for example, polymer) material, for example. The display 220 may be coupled to one surface of the support member 460, and the printed circuit board 480 may be coupled to the other surface thereof. A processor, a memory, and/or an interface may be mounted on the printed circuit board 480. The processor may include at least one of a central processing device, an application processor, a graphic processing unit (GPU), an application processor signal processing unit, or a communication processor, for example.

The memory may include, for example, a volatile memory or a nonvolatile memory. The interface may include, for example, a high-definition multimedia interface (HDMI), a universal serial bus (USB) interface, an SD card interface, and/or an audio interface. The interface may connect the electronic device 400 to an external electronic device electrically or physically, for example, and may include a USB connector, an SD card/MMC connector, or an audio connector.

The battery 470, which is a device for supplying power to at least one component of the electronic device 400, may include a primary battery that is not rechargeable, a secondary battery that is rechargeable, or a fuel cell, for example. At least a part of the battery 470 may be disposed on substantially the same plane as the printed circuit board 480, for example. The battery 470 may be integrally disposed inside the electronic device 200, or may be disposed such that the same can be attached to/detached from the electronic device 200.

The first antenna 450 may be disposed between the display 220 and the support member 460. The first antenna 450 may include, for example, a near-field communication (NFC) antenna, a wireless charging antenna, and/or a magnetic secure transmission (MST) antenna. The first antenna 450 may conduct short-range communication with an external device, for example, may wirelessly transmit/receive power utilized for charging, and may emit a magnetism-based signal including a short-range communication signal or payment data. In another embodiment, an antenna structure may be formed by a part or a combination of the side bezel structure 410 and/or the support member 460.

The second antenna 455 may be disposed between the circuit board 480 and the rear plate 493. The second antenna 455 may include, for example, a near-field communication (NFC) antenna, a wireless charging antenna, and/or a magnetic secure transmission (MST) antenna. The second antenna 455 may conduct short-range communication with an external device, for example, may wirelessly transmit/receive power utilized for charging, and may emit a magnetism-based signal including a short-range communication signal or payment data. In another embodiment, an antenna structure may be formed by a part or a combination of the side bezel structure 410 and/or the rear plate 493.

The sealing member 490 may be positioned between the side bezel structure 410 and the rear plate 493. The sealing member 490 may be configured to prevent external moisture and foreign substances from entering the space surrounded by the side bezel structure 410 and the rear plate 493.

Figure 5A:
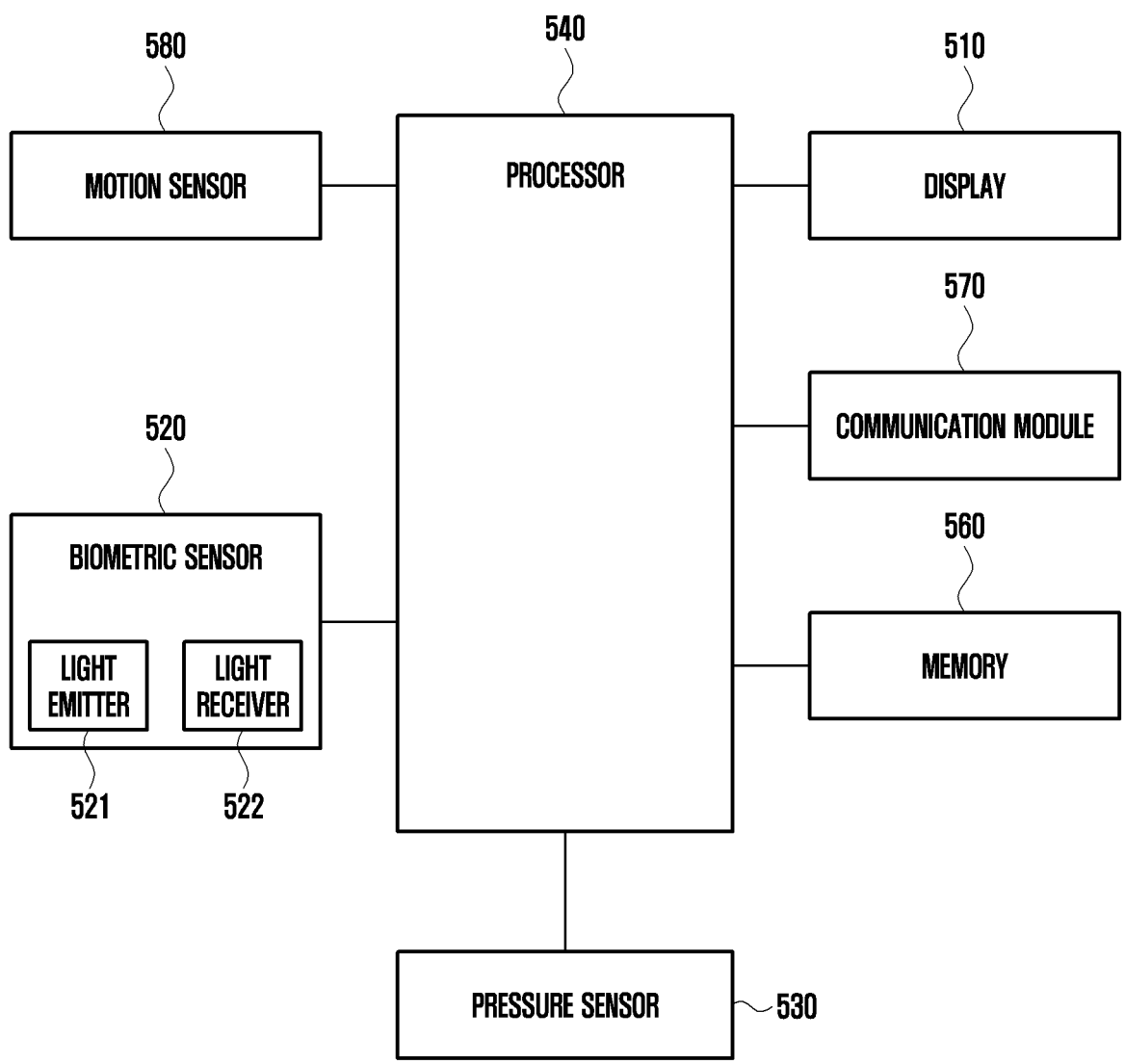
FIG. 5A is a block diagram of an electronic device according to certain embodiments disclosed in this document.
Figure 5B:
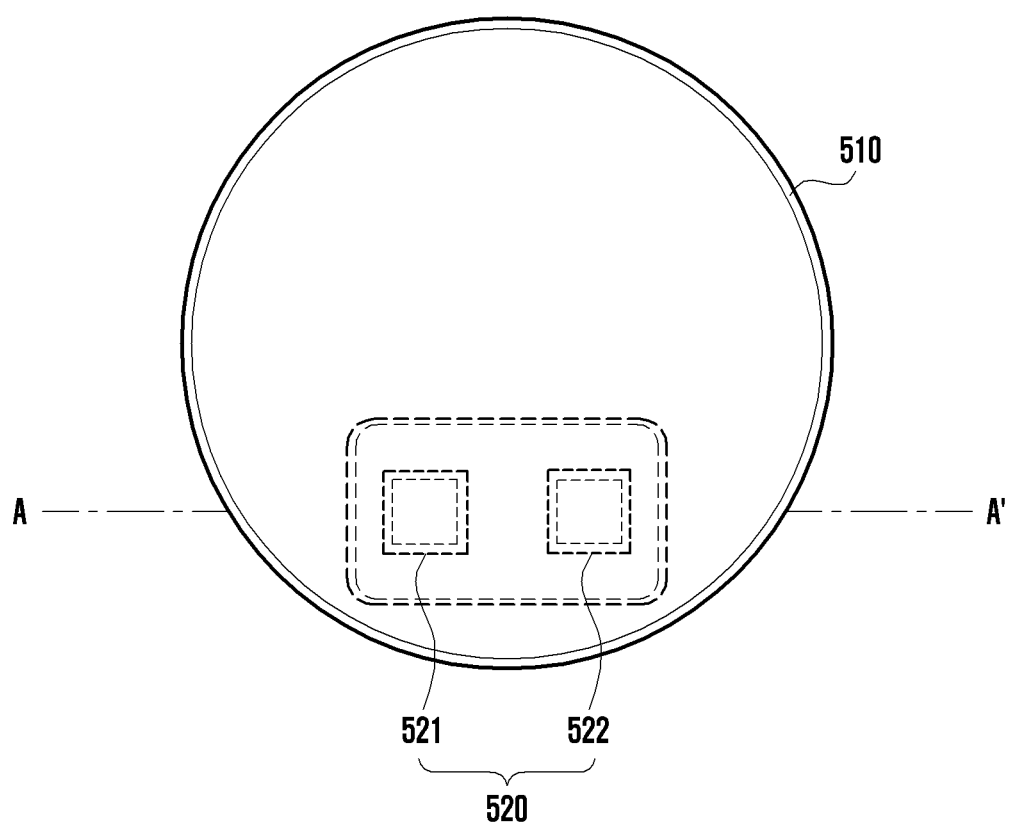
FIG. 5B is a schematic diagram of a biometric sensor, a pressure sensor, and peripheral components of the electronic device illustrated in FIG. 5A.
Figure 5C:
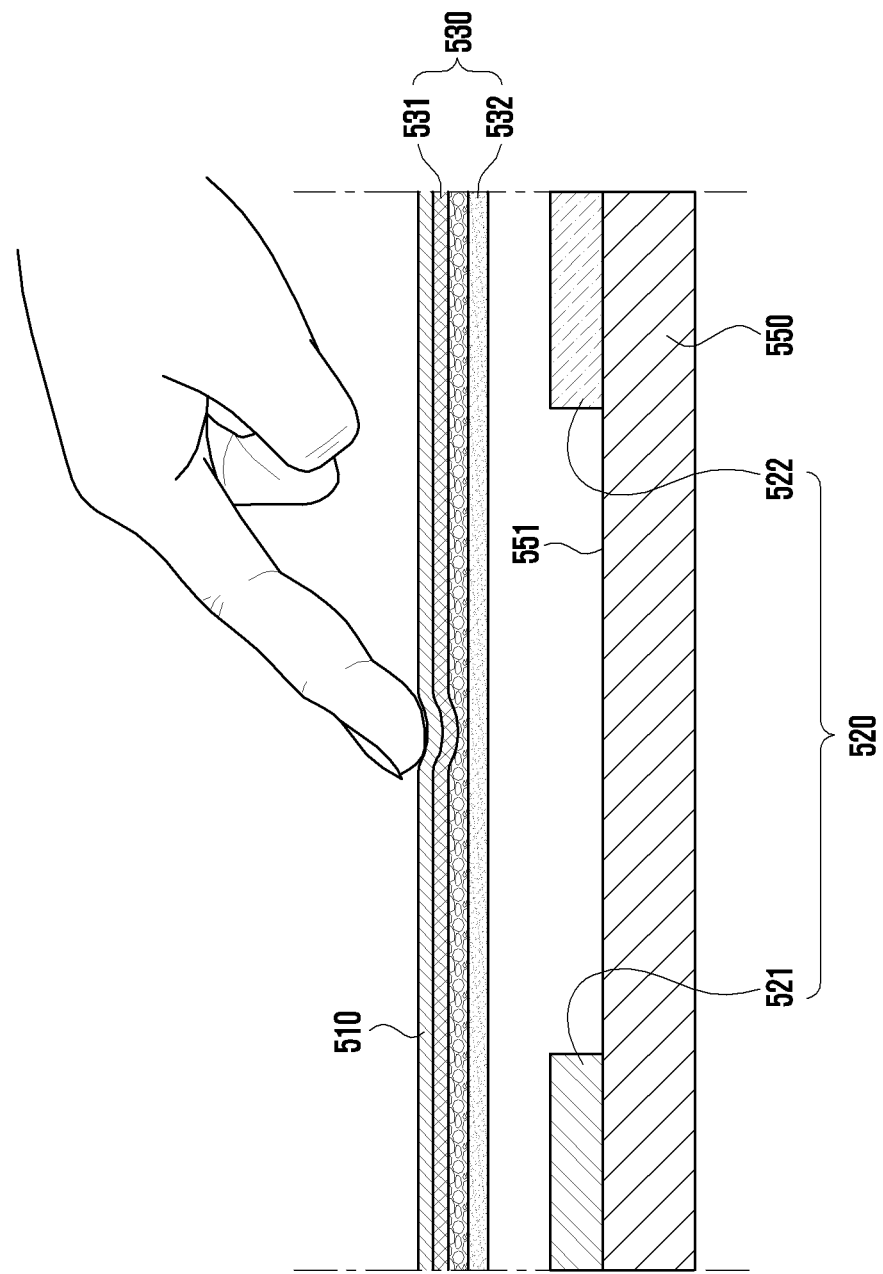
FIG. 5C is a sectional diagram taken along line A-A' in FIG. 5B.

FIG. 5A is a block diagram of an electronic device according to certain embodiments disclosed in this document. FIG. 5B is a schematic diagram of a biometric sensor, a pressure sensor, and peripheral components of the electronic device illustrated in FIG. 5A. FIG. 5C is a sectional diagram taken along line A-A' in FIG. 5B.

Referring to FIG. 5A, the electronic device according to certain embodiments disclosed in this document (for example, the electronic device 101 in FIG. 1 or the electronic device 200 or 400 in FIG. 2 to FIG. 4) may include: a display 510 (for example, the display device 160 in FIG. 1 or the display 220 in FIG. 4); a printed circuit board 550 (for example, the printed circuit board 480 in FIG. 4); a processor 540 (for example, the processor 120 in FIG. 1); a memory 560 (for example, the memory 130 in FIG. 1); a biometric module 520; a pressure sensor 530; a motion sensor 580; and a communication module 570 (for example, the communication module 190 in FIG. 1). The biometric sensor 520, the pressure sensor 530, and the motion sensor 580 may be sensors included in the sensor module 176 in FIG. 1 or the sensor module 211 in FIG. 3.

The electronic device illustrated in FIG. 5A to FIG. 5C may be a part of a mobile electronic device that is movable. Examples of such a mobile electronic device may include, for example, a smartphone, a tablet PC, and a laptop PC. According to certain embodiments, the electronic device illustrated in FIG. 5A to FIG. 5C may be a part of a wearable electronic device configured such that the same can be worn on a wrist, similarly to the electronic device 200 illustrated in FIG. 2. The configuration in FIG. 5A to FIG. 5C may be applied to various other types of electronic devices.

The display 510 may visually display information processed by the electronic device. Referring to FIG. 5B, the display 510 may be a circular display. According to certain embodiments, the shape of the display 510 is not limited to that illustrated in FIG. 5B, and may be variously modified according to the shape or usage of the electronic device. According to certain embodiments, the display 510 may be various types of displays 510 including a liquid crystal display (LCD) and an organic light-emitting diode (OLED). According to certain embodiments, the display 510 may be a flexible display that may allow bending.

The printed circuit board 550 may be disposed below the display 510, as illustrated in FIG. 5C. The description "below the display 510" refers to the direction opposite the direction in which the display 510 visually displays information. The printed circuit board 550 may include a first surface 551 facing the display 510. The biometric sensor 520 and the pressure sensor 530, described later, may be mounted on the first surface 551 of the printed circuit board 550. According to certain embodiments, the printed circuit board 550 may be a flexible printed circuit board (FPCB).

The biometric sensor 520 may be a sensor capable of sensing a biometric signal related to the user's heartbeat. The biometric sensor 520 may be mounted on the first surface 551 of the printed circuit board 550 and connected to the processor 540 electrically or operatively. As described above, the first surface 551 of the printed circuit board 550 faces the display 510, and the biometric sensor 520 may accordingly be disposed below the display 510 so as to face the display 510, as illustrated in FIG. 5C.

As described in FIG. 5B, the biometric sensor 520 may include a light emitter 521 configured to emit light and a light receiver 522 configured to receive light. The light emitter 521 may include one of a light-emitting diode (LED), an organic light-emitting diode (OLED), a laser diode (LD), a solid laser, and an infrared (IR) diode, which can emit light. The light emitter 521 may be made of various other elements capable of emitting light. The light receiver 522 may be a light-receiving element configured to convert optical energy into electric energy. Examples of such a light-receiving element may include, for example, one of a photodiode (PD), an avalanche photodiode (APD), and a phototransistor. The light receiver 522 may be made of various other elements capable of receiving light.

According to certain embodiments, multiple light receivers may be provided and disposed around the light emitter.

According to certain embodiments, a light source (for example, a backlight, LED, or OLED), which is the light-emitting component of the display 510, may be used to implement the light emitter of the biometric sensor. According to certain embodiments, the biometric sensor may be configured integrally with the display 510 in at least a partial region of the display 510.

While the user provides a gradually increasing/decreasing pressure to the display 510, the biometric sensor 520 may measure the user's pulse wave period and amplitude by using the light emitter 521 and the light receiver 522, thereby measuring a change in the pulse wave signal.

Hereinafter, operations of an electronic device measuring the user's pulse wave with the biometric sensor 520, including the light emitter 521 and the light receiver 522, will be described schematically.

The biometric sensor 520 may utilize a difference in an optical reaction resulting from the oxygen saturation level of hemoglobin in the blood. Light provided by the light emitter 521 may be transferred to the user's body through the display 510. The light receiver 522 may receive light transferred to the user's body and reflected therefrom. The reflected light may pass through the display 510 and enter the light receiver 522. The reflected light received by the light receiver 522 may have a periodicity due to a difference in the optical reaction resulting from the oxygen saturation level of hemoglobin described above. The electronic device may measure the user's pulse wave by using the periodicity acquired through the biometric sensor 520. The electronic device may measure the period and amplitude of the pulse wave through the biometric sensor 520. In some cases, the movement of the user may be indirectly measured through the motion sensor 580 of the electronic device, thereby processing a signal measured through the movement information more precisely. According to certain embodiments, the motion sensor 580 may be used to induce the position of the electronic device, which measures the user's pulse wave, to be maintained at the height of the user's heart.

The pulse wave measurement operation using the biometric sensor 520, described above, corresponds to a representative principle by which heartbeat-related information is sensed by using the light emitter 521 and the light receiver 522, and the electronic device according to certain embodiments disclosed in this document may measure the user's pulse wave through the biometric sensor 520 in various other methods.

The pressure sensor 530 may be a sensor capable of measuring the pressure applied to the display 510. The pressure sensor 530 may include an element capable of converting the pressure applied to the display 510 into an electric signal. For example, the pressure sensor 530 may be configured to measure a pressure by using a change in resistance/capacitance resulting from the pressure. According to certain embodiments, the pressure sensor 530 may be configured to include a piezoelectric element.

According to certain embodiments, the pressure sensor 530 may be configured to produce a pressure signal by sensing a change in the distance between two layers 531 and 532 disposed below the display 510 (e.g., by deformation of the display and layers, as illustrated in FIG. 5C). If the distance between the layers 531 and 532 is changed by the pressure applied to the display 510, the capacitance may change accordingly. The pressure sensor 530 may sense a change in the capacitance resulting from a change in the distance between the two layers 531 and 532, thereby measuring the degree of the applied pressure. The pressure sensor 530 may output a pressure signal corresponding to the pressure applied to the display 510.

The pressure sensor 530 may be disposed below the display 510 so as to face the display 510, thereby measuring the pressure applied to the display 510.

According to certain embodiments, the biometric sensor 520 and the pressure sensor 530 may be configured as a single module.

According to an embodiment, the processor 540 may be mounted on the printed circuit board 550. The processor 540, if mounted on the printed circuit board 550, may be electrically connected to the display 510, the biometric sensor 520, and the pressure sensor 530. The processor 540 may receive values measured by the biometric sensor 520 and the pressure sensor 530, and may transmit commands for operations of the biometric sensor 520 and the pressure sensor 530. The processor 540 may process values measured by the biometric sensor 520 and the pressure sensor 530 and may display the user's biometric information through the display 510.

Figure 5D:
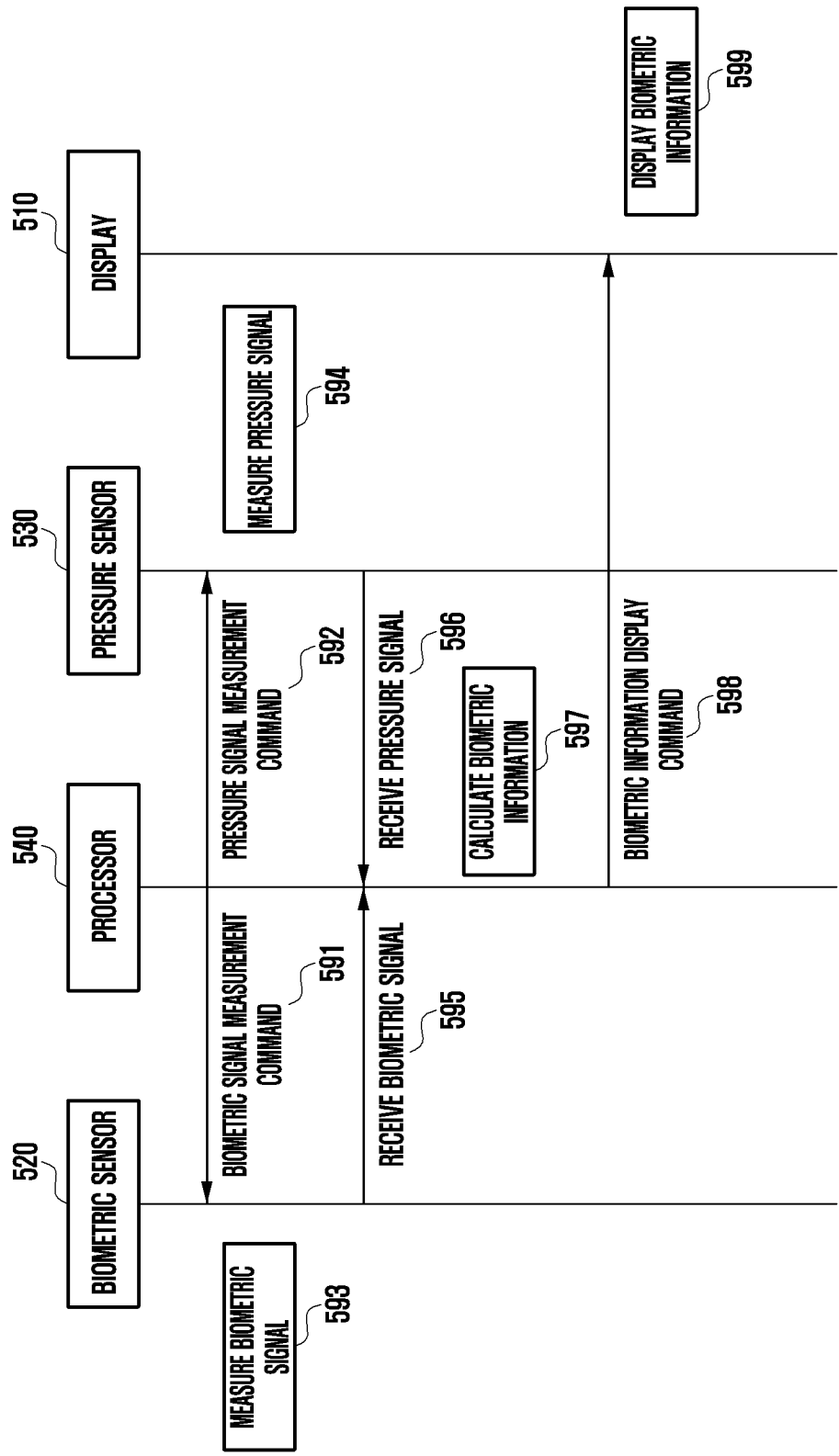
FIG. 5D is a flowchart illustrating operations of an electronic device according to certain embodiments displaying biometric information through a display.

FIG. 5D is a flowchart illustrating operations of an electronic device according to certain embodiments displaying biometric information through a display.

A processor 540 may perform or process a specific task according to an instruction stored in a memory 560.

According to certain embodiments, the processor 540 may transmit a biometric signal measurement command 591 to a biometric sensor 520. The biometric sensor 520 may perform a biometric signal measurement operation 593 based on the biometric signal measurement command 591. As used herein, a biometric signal may refer to the user's pulse wave signal measured by using a light emitter 521 and a light receiver 522. The processor 540 may receive (595) the biometric signal measured by the biometric sensor 520.

According to certain embodiments, the processor 540 may transmit a pressure signal measurement command 592 to a pressure sensor 530. The pressure sensor 530 may perform a pressure signal measurement operation 594 based on the pressure signal measurement command 592. As used herein, the pressure signal may refer to the pressure applied by the user through a display 510. The processor 540 may receive (596) the pressure signal measured by the pressure sensor 530.

According to certain embodiments, the processor 540 may calculate (597) biometric information by interlinking the biometric signal and the pressure signal. The processor 540 may transmit a biometric information display command to the display 510 in order to display the calculated biometric information through the display 510 (598). The display 510 may display (599) the biometric information based on the biometric information display command.

Figure 6:
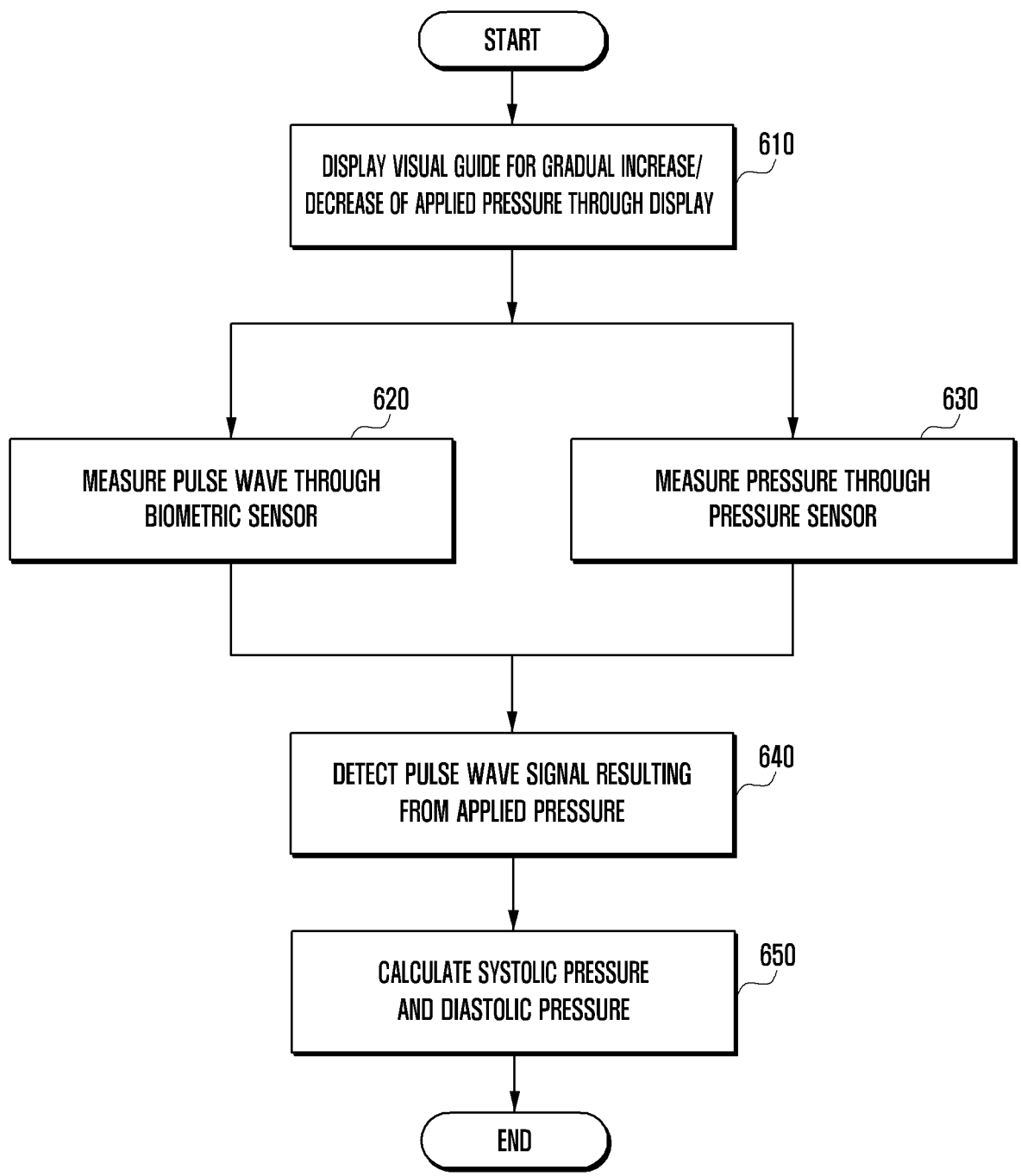
FIG. 6 is a flowchart of a method for measuring blood pressure by an electronic device according to certain embodiments disclosed in this document.

FIG. 6 is a flowchart of a method for measuring blood pressure by an electronic device according to certain embodiments disclosed in this document.

According to certain embodiments, measurement of the user's blood pressure may start in the following manner: the user inputs a blood pressure measurement start command through a display (for example, the display 510 in FIG. 5A), and a processor (for example, the processor 540 in FIG. 5A) receives the same. According to certain embodiments, the electronic device may periodically display a blood pressure measurement recommendation to the user through the display, thereby inducing the user to input a blood pressure measurement start command.

According to certain embodiments, if the user's pulse measured by a biometric sensor (for example, the biometric sensor 520 in FIG. 5A) is out of a normal range, the electronic device may start blood pressure measurement or may induce input of a blood pressure measurement start command.

According to certain embodiments, the operation 610 of displaying a visual guide prompting of the input of applied pressure through the display including a gradual increase and gradual decrease of the applied pressure. When blood pressure measurement is initiated, the processor may display a visual guide through the display to facilitate measurement. The visual guide may include a visual aid facilitating correct input of the pressure applied to the display through a part of the user's body, in a manner that increases/decreases gradually, which is utilized to execute the blood pressure reading. The visual guide may include a reference guide, the shape of which changes over time in order to help a user apply pressure to the display in the requested manner, and a recognition guide, the shape of which changes according to the degree of pressure applied to the display which informs a user as to how accurately he is inputting pressure for the blood pressure reading.

According to certain embodiments, operation 620 includes measuring the user's pulse wave through a biometric sensor having a light emitter (for example, the light emitter 521 in FIG. 5A) and a light receiver (for example, the light receiver 522 in FIG. 5A). The light emitted by the light emitter may propagate toward the user's skin, and the light reflected by the user's skin may enter the light receiver. The amount of light emitted by the light emitter and the amount of light received by the light receiver may be compared with each other, thereby measuring the user's pulse wave.

According to certain embodiments, operation 630 includes measuring a pressure through a pressure sensor (for example, the pressure sensor 530 in FIG. 5A), as applied to the display.

According to certain embodiments, operation 640 includes detecting a pulse wave signal following the applied pressure as measured from a biometric signal. As mentioned previously, the applied pressure may include application of a gradually increasing/decreasing pressure to the display, as prompted through a displayed visual guide. For example, the same may be an operation of detecting a pulse wave signal following a change in the applied pressure.

According to certain embodiments, the operation 650 may include calculating a systolic pressure and a diastolic pressure based on the relationship between the applied pressure and the pulse wave signal, as derived from detecting a pulse wave signal following the applied pressure.

Figure 7A:
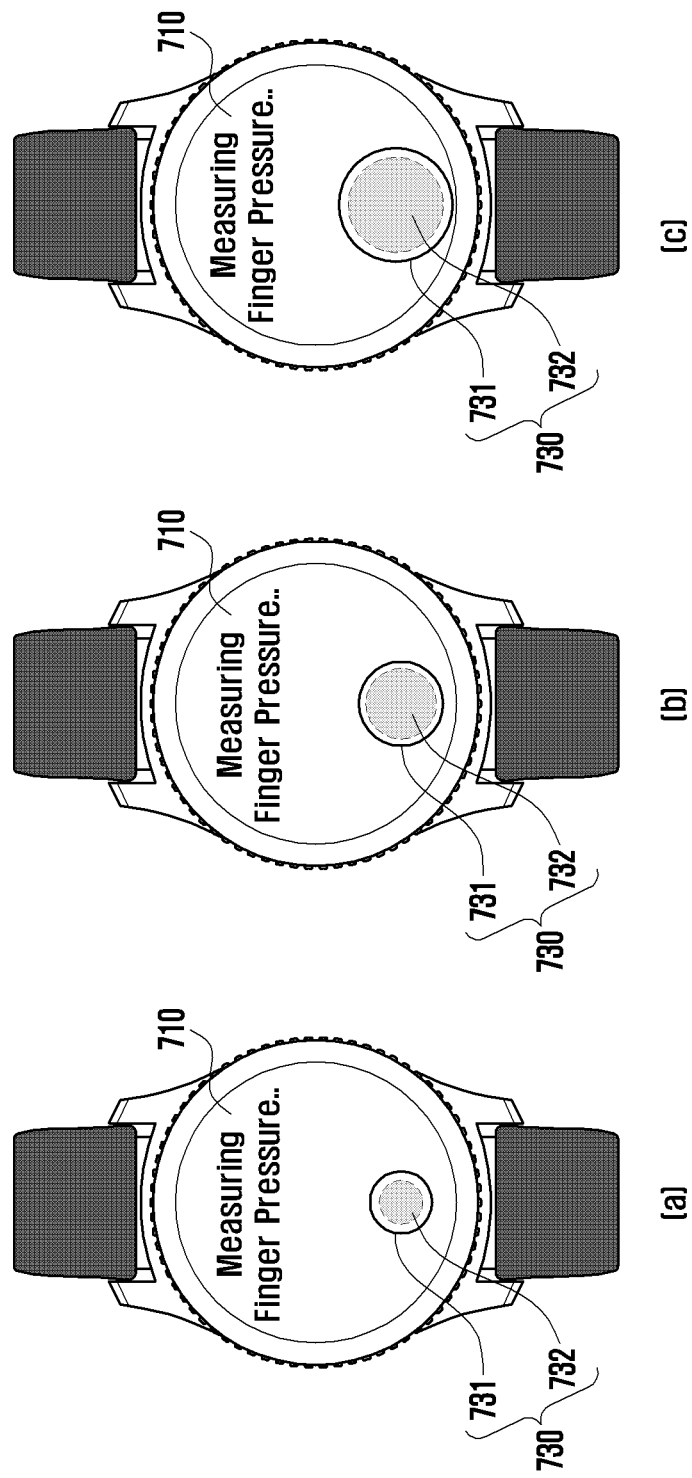
FIG. 7A(a) is a diagram for describing a visual guide of an electronic device according to certain embodiments, FIG. 7A(b) is a diagram for describing a visual guide of an electronic device according to certain embodiments, and FIG. 7A(c) is a diagram for describing a visual guide of an electronic device according to certain embodiments.

FIG. 7A(a) is a diagram for describing a visual guide of an electronic device according to certain embodiments, FIG. 7A(b) is a diagram for describing a visual guide of an electronic device according to certain embodiments, and FIG. 7A(c) is a diagram for describing a visual guide of an electronic device according to certain embodiments. FIG. 7B(a) is a diagram for describing a visual guide of an electronic device according to certain embodiments, and FIG. 7B(b) is a diagram for describing a visual guide of an electronic device according to certain embodiments.

According to certain embodiments, upon receiving a user input for starting blood pressure measurement, the electronic device (for example, the electronic device 101 in FIG. 1 or the electronic device 200 or 400 in FIG. 2 to FIG. 4) may display a visual guide through a display.

According to certain embodiments, as illustrated in FIG. 7A(a), FIG. 7A(b), and FIG. 7A(c), the visual guide 730 may include a circular reference guide 731 and a recognition guide 732, the centers of which are displayed in the same position. According to certain embodiments, a pressure sensor (for example, the pressure sensor 530 in FIG. 5C) may be located vertically below the center of the visual guide 730.

According to certain embodiments, the electronic device may control the diameter of the circular reference guide 731 so as to gradually change over time such that the pressure applied to the display 710 (for example, the display 510 in FIG. 5A) by a part of the user's body increases/decreases gradually. For example, in the case of inducing a gradual increase in the pressure applied to the display 710, the electronic device may control a corresponding gradual increase in the diameter of the reference guide 731 in the order of FIG. 7A(a), FIG. 7A(b), and FIG. 7A(c). For example, in the case of inducing a gradual decrease in the pressure applied to the display 710, the electronic device may control a corresponding gradual decrease in the diameter of the reference guide 731 in the order of FIG. 7A(c), FIG. 7A(b), and FIG. 7A(a).

According to certain embodiments, the electronic device may control the diameter of the recognition guide 732 so as to change according to the pressure applied to the display 710. For example, the electronic device may control the diameter of the recognition guide 732 to increase in proportion to the increasing pressure applied to the display 710. The user may identify the pressure applied by himself/herself to the display 710 in real time through the recognition guide 732. If the diameter of the recognition guide 732 is identical to the diameter of the reference guide 731, it may be determined that the requested pressure prompted by the electronic device has been applied. As described above, if the diameter of the reference guide 731 gradually increases/decreases over time, and if the recognition guide 732 follows the same change in the diameter of the reference guide 731, the pressure applied to the display 710 may be induced to increase/decrease to a predetermined level.

The user may adjust the applied pressure by adjusting the diameter of the recognition guide 732 to be identical to the diameter of the reference guide 731. As illustrated in FIG. 7B(a), if the diameter of the reference guide 731 is displayed smaller than the diameter of the recognition guide 732, the user may press the display 710 less strongly such that the diameter of the recognition guide 732 decreases. As illustrated in FIG. 7B(b), if the diameter of the reference guide 731 is displayed larger than the diameter of the recognition guide 732, the user may press the display 710 more strongly such that the diameter of the recognition guide 732 increases.

According to certain embodiments, if the diameter of the reference guide 731 and the diameter of the recognition guide 732 differ from each other, a guide message such as "Press more strongly" or "Press less strongly" may be shown through the display 710.

According to certain embodiments, the color of the reference guide 731 may be changed according to whether the difference between the diameter of the reference guide 731 and the diameter of the recognition guide 732 is maintained within a prestored range or deviates from the prestored range. For example, the color of the reference guide 731 may be green if the difference between the diameter of the reference guide 731 and the diameter of the recognition guide 732 is maintained within the prestored range. The color of the reference guide 731 may turn red if the difference between the diameter of the reference guide 731 and the diameter of the recognition guide 732 deviates from the prestored range.

According to certain embodiments, the electronic device may provide the user with haptic feedback such that the difference between the diameter of the reference guide 731 and the diameter of the recognition guide 732 is maintained within the prestored range. For example, haptic feedback may be provided if the diameter of the reference guide 731 and the diameter of the recognition guide 732 are identical. No haptic feedback may be provided if the diameter of the recognition guide 732 is smaller than the diameter of the reference guide 731. The intensity or frequency of the haptic feedback may be changed if the diameter of the recognition guide 732 is larger than the diameter of the reference guide 731. This may induce the user to apply gradually increasing/decreasing pressure to the display.

FIG. 8(*a*) is a diagram for describing a visual guide of an electronic device according to certain embodiments, FIG. 8(*b*) is a diagram for describing a visual guide of an electronic device according to certain embodiments, and FIG. 8(*c*) is a diagram for describing a visual guide of an electronic device according to certain embodiments.

According to certain embodiments, as illustrated in FIG. 8(*a*), FIG. 8(*b*), and FIG. 8(*c*), the visual guide 830 may include a reference guide 831 and a recognition guide 832, which are displayed in rod shapes.

According to certain embodiments, the electronic device may control the length of the rod-shaped reference guide 831 so as to gradually change over time such that the pressure applied to the display 810 (for example, the display 510 in FIG. 5A) by a part of the user's body increases/decreases gradually. For example, in the case of inducing a gradual increase in the pressure applied to the display 810, the electronic device may control an increase in the length of the reference guide 831 in the order of FIG. 8(*a*), FIG. 8(*b*), and FIG. 8(*c*). For example, in the case of inducing a gradual decrease in the pressure applied to the display 810, the electronic device may control a decrease in the length of the reference guide 831 in the order of FIG. 8(*c*), FIG. 8(*b*), and FIG. 8(*a*).

According to certain embodiments, the electronic device may control the length of the recognition guide 832 so as to change according to the pressure applied to the display 810. For example, the electronic device may control the length of the recognition guide 832 so as to increase in proportion to the increasing pressure applied to the display 810. The user may identify the pressure applied by himself/herself to the display 810 in real time through the recognition guide 832. If the length of the recognition guide 832 is identical to the length of the reference guide 831, it may be determined that the pressure desired by the electronic device has been applied. As described above, if the length of the reference guide 831 gradually increases/decreases over time, and if the recognition guide 832 follows the same change in the length of the reference guide 831, the pressure applied to the display 810 may be induced to increase/decrease to a predetermined level. According to certain embodiments, the level of the pressure currently applied to the display 810 may be converted into a numerical value, which may be displayed (840) in real time.

Although a circular visual guide (for example, the visual guide 730 in FIG. 7A) and a rod-shaped visual guide (for example, the visual guide 830 in FIG. 8(*a*)) have been described above as examples of the visual guide, the shape of the visual guide may be variously modified such that the user is induced to apply gradually increasing/decreasing pressure to the display. For example, the visual guide may have a donut shape, a gauge shape, a pulse shape, or the like.

Figure 9:
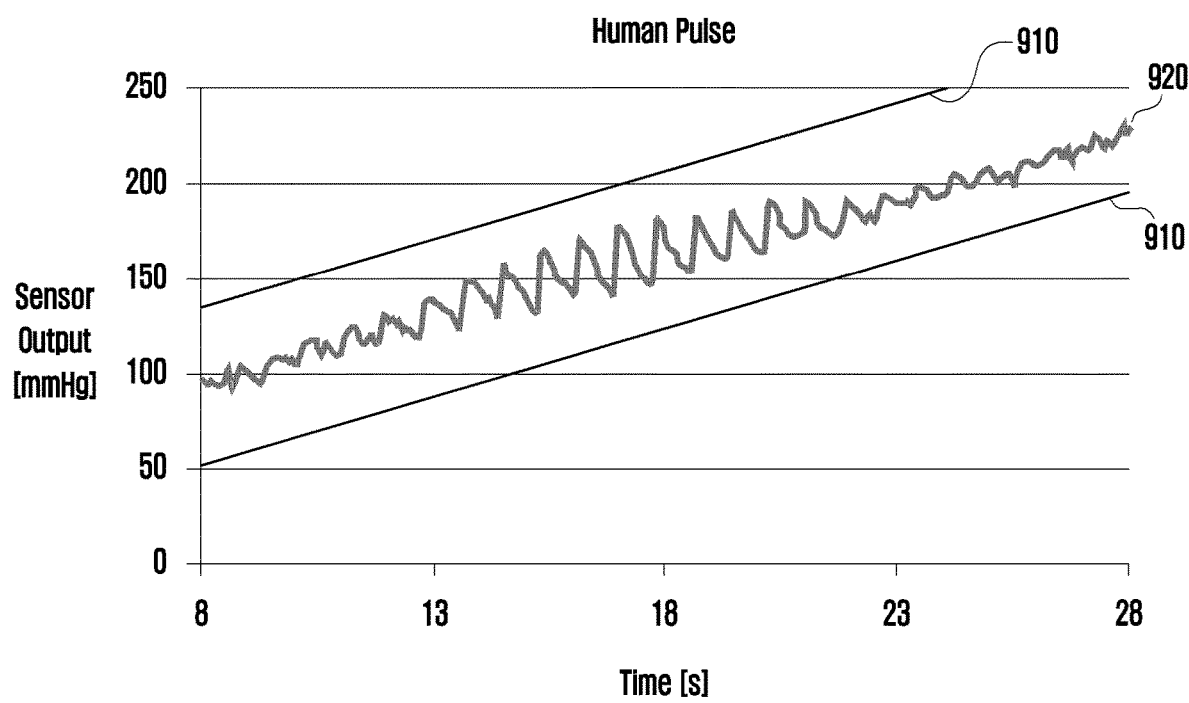
FIG. 9 is a graph illustrating a pulse wave change following a gradually increasing/decreasing pressure according to certain embodiments.

FIG. 9 is a graph illustrating a pulse wave change 920 following a gradually increasing/decreasing pressure according to certain embodiments.

According to certain embodiments, the pulse wave change 920 may correspond to a pulse wave change measured by a biometric sensor (for example, biometric sensor 520 in FIG. 5A) with regard to the pressure measured by a pressure sensor (for example, the pressure sensor 530 in FIG. 5A), and plotted over time.

As described above, the pressure applied to the display may constantly increase/decrease in a predetermined range 910 by means of the visual guide (for example, the visual guide 730 in FIG. 7A or the visual guide 830 in FIG. 8(*a*)) displayed through the display (for example, the display 710 in FIG. 7A or the display 810 in FIG. 8(*a*)). The processor (for example, the processor 540 in FIG. 5A) may calculate the user's blood pressure by interlinking a pressure signal measured by the pressure sensor (for example, the pressure sensor 530 in FIG. 5A) and a pulse wave signal measured by the biometric sensor (for example, the biometric sensor 520 in FIG. 5A). According to certain embodiments, the processor may calculate the user's blood pressure by using various algorithms.

Figure 10:
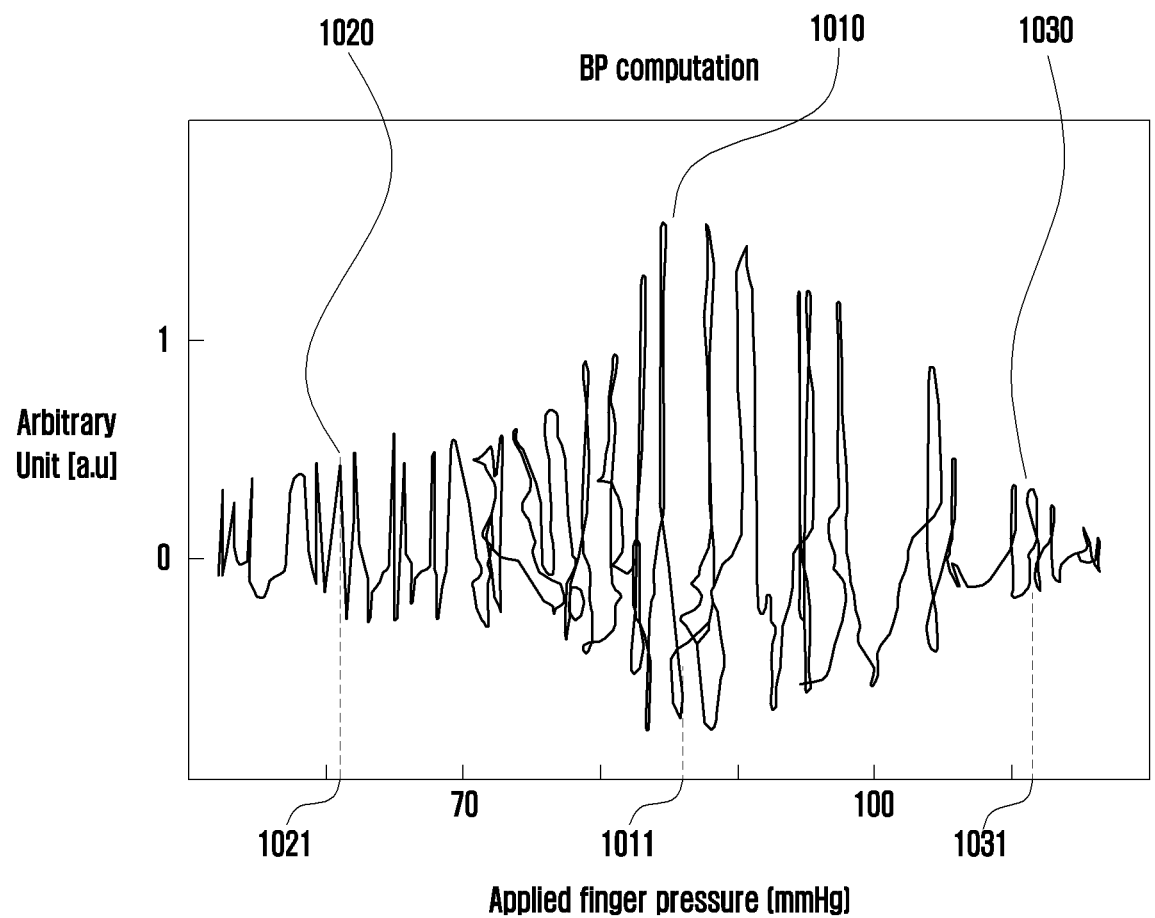
FIG. 10 is a graph illustrating a variation width of a pulse wave signal magnitude following an applied pressure according to certain embodiments.

FIG. 10 is a graph illustrating a variation width of a pulse wave signal magnitude following an applied pressure according to certain embodiments.

According to certain embodiments, a processor (for example, the processor 540 in FIG. 5A) may calculate a diastolic pressure and a systolic pressure by using a reference variation value.

For example, the processor may receive a gradually increasing pressure signal and may receive a change in a pulse wave signal measured by a biometric sensor (for example, the biometric sensor 520 in FIG. 5A) according to the pressure signal. In this case, the pulse wave signal may propagate in the rightward direction in FIG. 10. When the variation width of the pulse wave signal following the gradually increasing pressure signal reaches a first reference value 1020, or when the variation width of the pulse wave signal following the pressure signal satisfies the first reference value 1020 at least a configured number of times, a first measurement value 1021 measured by the pressure sensor 530 may be determined as a diastolic pressure. As another example, when the average of variation widths of pulse wave signals measured in a specific interval reaches a first reference value 1020, the average value or intermediate value of pressure signals measured through the pressure sensor 530 in the corresponding interval may be determined as a diastolic pressure. When the variation width of a pulse wave signal following a gradually increasing pressure signal reaches a second reference value 1030 past the first measurement value 1021, or when the variation width of the pulse wave signal following the pressure signal satisfies the second reference value 1030 at least a configured number of times, a second measurement value 1031 measured by the pressure sensor 530 may be determined as a systolic pressure. As another example, when the average of variation widths of pulse wave signals measured in a specific interval reaches a second reference value 1030, the average value or intermediate value of pressure signals measured through the pressure sensor 530 in the corresponding interval may be determined as a systolic pressure. With reference to FIG. 10, the first measurement value 1021 is approximately 63 mmHg and the second measurement value 1031 is approximately 112 mmHg. Accordingly, it may be determined that the diastolic pressure is 63 mmHg, and the systolic pressure is 112 mmHg. According to certain embodiments, when the variation width of a pulse wave signal reaches the maximum value, the pressure value measured by the pressure sensor may be identified, and re-measurement may be executed if the value is not clearly specified.

For example, the processor may receive a gradually decreasing pressure signal and may receive a change in a pulse wave signal measured by the biometric sensor according to the pressure signal. In this case, the pulse wave signal may propagate in the leftward direction in FIG. 10. When the variation width of the pulse wave signal following the gradually decreasing pressure signal reaches a second reference value 1030, or when the variation width of the pulse wave signal following the pressure signal satisfies the second reference value 1030 at least a configured number of times, a second measurement value 1031 measured by the pressure sensor 530 may be determined as a diastolic pressure. As another example, when the average of variation widths of pulse wave signals measured in a specific interval reaches a second reference value 1030, the average value or intermediate value of pressure signals measured through the pressure sensor 530 in the corresponding interval may be determined as a diastolic pressure. When the variation width of a pulse wave signal following a gradually decreasing pressure signal reaches a first reference value 1020 past the second measurement value 1031, or when the variation width of the pulse wave signal following the pressure signal satisfies the first reference value 1020 at least a configured number of times, a first measurement value 1021 measured by the pressure sensor 530 may be determined as a diastolic pressure. As another example, when the average of variation widths of pulse wave signals measured in a specific interval reaches a first reference value 1020, the average value or intermediate value of pressure signals measured through the pressure sensor 530 in the corresponding interval may be determined as a diastolic pressure. With reference to FIG. 10, the first measurement value 1021 is approximately 63 mmHg, and the second measurement value 1031 is approximately 112 mmHg. Accordingly, it may be determined that the diastolic pressure is 63 mmHg, and the systolic pressure is 112 mmHg. According to certain embodiments, when the variation width of a pulse wave signal reaches the maximum value, the pressure value measured by the pressure sensor may be identified, and re-measurement may be executed if the value is not clearly specified.

According to certain embodiments, the processor may determine that a pressure signal at a point 1010 having the largest variation width of a pulse wave signal is a reference pressure value 1011, and may estimate a systolic pressure and a diastolic pressure with reference to the pressure value 1011.

For example, the processor may estimate that a pressure value at a point at which a reference pressure value 1011 is identical to a variation width obtained by multiplying a variation width of a measured pulse wave signal by a preconfigured first ratio is a diastolic pressure. The processor may estimate that a pressure value at a point at which a reference pressure value 1011 is identical to a variation width obtained by multiplying a variation width of a measured pulse wave signal by a preconfigured second ratio is a systolic pressure.

For example, the processor may estimate that a pressure value obtained by multiplying a reference pressure value 1011 by a third ratio is a diastolic pressure and that a pressure value obtained by multiplying the reference pressure value 1011 by a fourth ratio is a systolic pressure.

According to certain embodiments, the first to fourth ratios may be configured by using the user's blood pressure data measured by a cuff blood pressure gauge using an oscillometric measurement method.

In addition, the processor may calculate the blood pressure by using various algorithms utilizing a change in a pulse wave signal following a gradually increasing/decreasing pressure signal.

An electronic device according to certain embodiments disclosed in this document may include: a display; a printed circuit board disposed below the display and having a first surface facing the display; a biometric sensor disposed in at least one region of the first surface of the printed circuit board so as to measure a biometric signal related to a heartbeat; a pressure sensor disposed below the display so as to measure a pressure applied to the display; a processor operatively connected to the display, the biometric sensor, and the pressure sensor; and a memory operatively connected to the processor. The memory may store instructions that, when executed, cause the processor to: cause the biometric sensor to measure a biometric signal; cause the pressure sensor to measure a pressure signal; receive the biometric signal from the biometric sensor and receive the pressure signal from the pressure sensor; calculate biometric information related to a heartbeat by interlinking the biometric signal and the pressure signal; and output the biometric information to the display.

In addition, the biometric sensor may include a light emitter configured to emit light toward the display and a light receiver configured to receive light reflected by a user's body.

In addition, the instructions may cause the processor to receive a gradually increasing/decreasing pressure signal from the pressure sensor and receive a change in a pulse wave signal measured by the biometric sensor according to the pressure signal, thereby measuring blood pressure.

In addition, the instructions may cause the processor to: determine that a pressure signal measured by the pressure sensor is a reference pressure value when a variation width of the pulse wave signal measured by the biometric sensor is largest; and estimate a diastolic pressure and a systolic pressure by using the reference pressure value.

In addition, the instructions may cause the processor to: receive a gradually increasing pressure signal from the pressure sensor; receive a change in a pulse wave signal measured by the biometric sensor according to the pressure signal; determine that, when a variation width of the pulse wave signal following the gradually increasing pressure signal reaches a first reference value, a first measurement value measured by the pressure sensor is a diastolic pressure; and determine that, when the variation width of the pulse wave signal following the gradually increasing pressure signal reaches a second reference value past the first measurement value, a second measurement value measured by the pressure sensor is a systolic pressure.

In addition, the instructions may cause the processor to: receive a gradually increasing pressure signal from the pressure sensor; receive a change in a pulse wave signal measured by the biometric sensor according to the pressure signal; determine that, when the number of times a variation width of the pulse wave signal following the gradually increasing pressure signal reaches a first reference value satisfies a configured number, a first measurement value measured by the pressure sensor is a diastolic pressure; and determine that, when the number of times the variation width of the pulse wave signal following the gradually increasing pressure signal reaches a second reference value past the first measurement value satisfies a configured number, a second measurement value measured by the pressure sensor is a systolic pressure.

In addition, the instructions may cause the processor to: receive a gradually decreasing pressure signal from the pressure sensor; receive a change in a pulse wave signal measured by the biometric sensor according to the pressure signal; determine that, when a variation width of the pulse wave signal following the gradually decreasing pressure signal reaches a second reference value, a second measurement value measured by the pressure sensor is a systolic pressure; and determine that, when the variation width of the pulse wave signal following the gradually decreasing pressure signal reaches a first reference value past the second measurement value, a first measurement value measured by the pressure sensor is a diastolic pressure.

In addition, the instructions may cause the processor to: receive a gradually decreasing pressure signal from the pressure sensor; receive a change in a pulse wave signal measured by the biometric sensor according to the pressure signal; determine that, when the number of times a variation width of the pulse wave signal following the gradually decreasing pressure signal reaches a second reference value satisfies a configured number, a second measurement value measured by the pressure sensor is a systolic pressure; and determine that, when the number of times the variation width of the pulse wave signal following the gradually decreasing pressure signal reaches a first reference value past the second measurement value satisfies a configured number, a first measurement value measured by the pressure sensor is a diastolic pressure.

In addition, the biometric sensor and the pressure sensor may be configured as a single sensor module.

In addition, the instructions may cause the processor to display a visual guide through the display such that a pressure applied to the display increases/decreases gradually.

In addition, the visual guide may include: a reference guide having a shape changing over time such that the pressure applied to the display increases/decreases by a preconfigured degree; and a recognition guide having a shape changing according to the degree of the pressure applied to the display, the recognition guide being displayed in a shape corresponding to the reference guide.

In addition, the reference guide of the visual guide may have the shape of a circle having a diameter changing over time, and the recognition guide of the visual guide may have the shape of a circle having a diameter changing according to a pressure signal measured by the pressure sensor.

In addition, the reference guide of the visual guide may have the shape of a rod having a length changing over time, and the recognition guide of the visual guide may have the shape of a rod having a length changing according to a pressure signal measured by the pressure sensor.

A method for measuring a user's blood pressure by using a biometric sensor and a pressure sensor disposed below a display of an electronic device according to certain embodiments disclosed in this document may include the operations of: displaying a visual guide through the display of the electronic device such that a pressure signal measured by the pressure sensor configured to measure a pressure applied to the display increases/decreases gradually; measuring a gradually increasing/decreasing pressure signal by using the pressure sensor, and measuring a change in a pulse wave signal by using the biometric sensor; detecting a change in the pulse wave signal following the pressure signal; and calculating the user's blood pressure by using the change in the pulse wave signal following the pressure signal.

In addition, the biometric sensor and the pressure sensor may be disposed in at least one region of a first surface of a printed circuit board disposed below the display such that the first surface faces the display.

In addition, the biometric sensor may include a light emitter configured to emit light toward the display and a light receiver configured to receive light reflected by the user's body.

In addition, the visual guide displayed through the display may include: a reference guide having a shape changing over time such that the pressure applied to the display increases/decreases by a preconfigured degree; and a recognition guide having a shape changing according to the degree of the pressure applied to the display, the recognition guide being displayed in a shape corresponding to the reference guide.

In addition, the reference guide of the visual guide may have the shape of a circle having a diameter changing over time, and the recognition guide of the visual guide may have the shape of a circle having a diameter changing according to a pressure signal measured by the pressure sensor.

In addition, the reference guide of the visual guide may have the shape of a rod having a length changing over time, and the recognition guide of the visual guide may have the shape of a rod having a length changing according to a pressure signal measured by the pressure sensor.

In addition, the operation of calculating the user's blood pressure may include the operations of: determining that, when a variation width of the pulse wave signal measured by the biometric sensor is largest, the pressure signal measured by the pressure sensor is a reference pressure value; and estimating a diastolic pressure and a systolic pressure by using the reference pressure value.

In addition, the operation of calculating the user's blood pressure may include the operations of: determining that, when a variation width of the pulse wave signal following the gradually increasing pressure signal reaches a first reference value, a first measurement value measured by the pressure sensor is a diastolic pressure; and determining that, when the variation width of the pulse wave signal following the gradually increasing pressure signal reaches a second reference value past the first measurement value, a second measurement value measured by the pressure sensor is a systolic pressure.

In addition, the operation of calculating the user's blood pressure may include the operations of: determining that, when a variation width of the pulse wave signal following the gradually decreasing pressure signal reaches a second reference value, a second measurement value measured by the pressure sensor is a systolic pressure; and determining that, when the variation width of the pulse wave signal following the gradually decreasing pressure signal reaches a first reference value past the second measurement value, a first measurement value measured by the pressure sensor is a diastolic pressure.

Furthermore, embodiments disclosed in the specification and illustrated in the drawings are merely specific examples presented to easily describe the technical content of the disclosed embodiments and to help understanding thereof, and are not intended to limit the breadth of the disclosed embodiments. Therefore, the breadth of certain embodiments disclosed in this document is to be interpreted as encompassing all modifications or modified forms derived based on the technical idea of the certain embodiments disclosed in this document, besides the embodiments disclosed herein.

What is claimed is:

1. An electronic device comprising:
   a display;
   a printed circuit board (PCB) disposed below the display and having a first surface facing the display;
   a biometric sensor disposed on the first surface of the PCB and configured to measure a biometric signal related to a heartbeat;
   a pressure sensor disposed below the display and configured to generate a pressure signal based on measuring a pressure applied to the display;

a processor operatively connected to the display, the biometric sensor, and the pressure sensor; and a memory operatively connected to the processor, wherein the memory stores instructions that, when executed, cause the processor to:

display, through the display, a visual guide prompting a user to gradually increase or decrease the pressure applied to the display;

measure, by the biometric sensor, the biometric signal;

measure, by the pressure sensor, the pressure applied to the display;

receive the biometric signal from the biometric sensor and receive the pressure signal from the pressure sensor;

calculate biometric information related to a heartbeat by interlinking the biometric signal and the pressure signal; and output the calculated biometric information to the display, wherein the visual guide is displayed on an area of the display including a perimeter of an area pressed by the user and comprises:

a reference guide including display of a first shape that changes over time to prompt the user to gradually increase or decrease the pressure at a preconfigured degree; and a recognition guide including display of a second shape that changes according to the degree of the pressure applied to the display, wherein display of the recognition guide corresponds to display of the reference guide.

2. The electronic device of claim 1, wherein the biometric sensor comprises a light emitter configured to emit light toward the display, and a light receiver configured to receive the emitted light reflected by a user's body back towards the biometric sensor.

3. The electronic device of claim 1, wherein the instructions are configured to cause the processor to receive a gradually increasing or decreasing pressure signal from the pressure sensor and to receive a change in a pulse wave signal measured by the biometric sensor according to the pressure signal, thereby measuring blood pressure.

4. The electronic device of claim 3, wherein the instructions are configured to cause the processor to:

set that the pressure signal as a reference pressure value when a variation width of the pulse wave signal is at a maximum value; and estimate a diastolic pressure and a systolic pressure using the reference pressure value.

5. The electronic device of claim 1, wherein the instructions are configured to cause the processor to:

receive a gradually increasing pressure signal from the pressure sensor;

receive a change in a pulse wave signal measured by the biometric sensor according to the pressure signal;

determine that, when a variation width of the pulse wave signal following the gradually increasing pressure signal reaches a first reference value, a first measurement value measured by the pressure sensor is a diastolic pressure; and determine that, when the variation width of the pulse wave signal following the gradually increasing pressure signal reaches a second reference value past the first measurement value, a second measurement value measured by the pressure sensor is a systolic pressure.

6. The electronic device of claim 1, wherein the instructions are configured to cause the processor to:

receive a gradually increasing pressure signal from the pressure sensor;

receive a change in a pulse wave signal measured by the biometric sensor according to the pressure signal;

determine that, when the number of times a variation width of the pulse wave signal following the gradually increasing pressure signal reaches a first reference value satisfies a configured number, a first measurement value measured by the pressure sensor is a diastolic pressure; and determine that, when the number of times the variation width of the pulse wave signal following the gradually increasing pressure signal reaches a second reference value past the first measurement value satisfies a configured number, a second measurement value measured by the pressure sensor is a systolic pressure.

7. The electronic device of claim 1, wherein the instructions are configured to cause the processor to:

receive a gradually decreasing pressure signal from the pressure sensor;

receive a change in a pulse wave signal measured by the biometric sensor according to the pressure signal;

determine that, when a variation width of the pulse wave signal following the gradually decreasing pressure signal reaches a second reference value, a second measurement value measured by the pressure sensor is a systolic pressure, and determine that, when the variation width of the pulse wave signal following the gradually decreasing pressure signal reaches a first reference value past the second measurement value, a first measurement value measured by the pressure sensor is a diastolic pressure.

8. The electronic device of claim 1, wherein the instructions are configured to cause the processor to:

receive a gradually decreasing pressure signal from the pressure sensor;

receive a change in a pulse wave signal measured by the biometric sensor according to the pressure signal;

determine that, when the number of times a variation width of the pulse wave signal following the gradually decreasing pressure signal reaches a second reference value satisfies a configured number, a second measurement value measured by the pressure sensor is a systolic pressure; and determine that, when the number of times the variation width of the pulse wave signal following the gradually decreasing pressure signal reaches a first reference value past the second measurement value satisfies a configured number, a first measurement value measured by the pressure sensor is a diastolic pressure.

9. The electronic device of claim 1, wherein the biometric sensor and the pressure sensor are included in a single sensor module.

10. The electronic device of claim 1, wherein the first shape of the reference guide includes a first circle having a diameter that changes over time, and wherein the second shape of the recognition guide includes a second circle having a diameter that changes according to the pressure signal measured by the pressure sensor.

11. The electronic device of claim 1, wherein the first shape of the reference guide includes a first rod having a length that changes over time, and the second shape of the visual guide includes a second rod having a length that changes according to the pressure signal measured by the pressure sensor.

12. A method for an electronic device, the method comprising:
- measuring, using a pressure sensor, a pressure signal based on pressure applied to a display;
- displaying, using a display, a visual guide prompting a user generating the pressure to gradually increase and decrease the pressure;
- while the pressure gradually increases or decreases, measuring a change in a biometric signal related to a heartbeat using a biometric sensor, including a pulse wave signal;
- detecting a change in the pulse wave signal while the pressure gradually increases or decreases; and
- calculating the user's blood pressure based on the detected change in the pulse wave signal while the pressure gradually increases or decreases,
- wherein the visual guide is displayed on an area of the display including a perimeter of an area pressed by the user and comprises: a reference guide including display of a first shape that changes over time to prompt the user to gradually increase or decrease the pressure at a preconfigured degree, and a recognition guide including display of a second shape that changes according to the degree of the pressure applied to the display, and
- wherein display of the recognition guide corresponds to display of the reference guide.

13. The method of claim 12, wherein the biometric sensor and the pressure sensor are disposed on a first surface of a printed circuit board (PCB), below the display, and
- wherein the first surface faces the display.

14. The method of claim 12, wherein the biometric sensor comprises a light emitter configured to emit light toward the display, and a light receiver configured to receive the emitted light reflected by a user's body back towards the biometric sensor.

15. The method of claim 12, wherein the first shape of the reference guide includes a first circle having a diameter that changes over time, and
- wherein the second shape of the recognition guide includes a second circle having a diameter that changes according to the pressure signal measured by the pressure sensor.

16. The method of claim 12, wherein the first shape of the reference guide includes a first rod having a length that changes over time, and
- wherein the second shape of the visual guide includes a second rod having a length that changes according to the pressure signal measured by the pressure sensor.

17. The method of claim 12, wherein the calculating the user's blood pressure comprises:
- when a variation width of the pulse wave signal is at a maximum value, setting the pressure signal at a time of the maximum value as a reference pressure value; and
- estimating a diastolic pressure and a systolic pressure using the reference pressure value.

\* \* \* \* \*